United States Patent
Xie et al.

(10) Patent No.: US 10,858,312 B1
(45) Date of Patent: Dec. 8, 2020

(54) GOSSYPOL ISOCYANATE ESTER COMPOUNDS WITH ANTILEUKEMIC ACTIVITIES AND A METHOD OF PREPARING THE SAME

(71) Applicants: Xiaolin Xie, Xi'an (CN); Dezhu Zhang, Xi'an (CN); Zhong Meng, Xi'an (CN); Jianguo Meng, Xi'an (CN); Yu Wang, Xi'an (CN); Shunjun Ding, Xi'an (CN); Chengyuan Liang, Xi'an (CN); Liang Xin, Xi'an (CN); Jingyi Li, Xi'an (CN); Jiayun Zhang, Xi'an (CN); Kangxiong Wu, Xi'an (CN); Juan Xia, Xi'an (CN); Han Li, Xi'an (CN)

(72) Inventors: Xiaolin Xie, Xi'an (CN); Dezhu Zhang, Xi'an (CN); Zhong Meng, Xi'an (CN); Jianguo Meng, Xi'an (CN); Yu Wang, Xi'an (CN); Shunjun Ding, Xi'an (CN); Chengyuan Liang, Xi'an (CN); Liang Xin, Xi'an (CN); Jingyi Li, Xi'an (CN); Jiayun Zhang, Xi'an (CN); Kangxiong Wu, Xi'an (CN); Juan Xia, Xi'an (CN); Han Li, Xi'an (CN)

(73) Assignee: SHAANXI PANLONG PHARMACEUTICAL GROUP LIMITED BY SHARE LTD., Xi'an (CN)

( * ) Notice: Subject to any disclaimer, the term of this patent is extended or adjusted under 35 U.S.C. 154(b) by 0 days.

(21) Appl. No.: 16/939,766

(22) Filed: Jul. 27, 2020

(30) Foreign Application Priority Data

Jul. 8, 2020 (CN) .......................... 2020 1 0654056

(51) Int. Cl.
C07C 271/02 (2006.01)
C07C 269/06 (2006.01)

(52) U.S. Cl.
CPC .......... C07C 271/02 (2013.01); C07C 269/06 (2013.01)

(58) Field of Classification Search
CPC ... C07C 271/02; C07C 271/06; C07C 271/10; C07C 271/26; C07C 271/38; C07C 269/06
See application file for complete search history.

(56) References Cited

U.S. PATENT DOCUMENTS 3,953,260 A * 4/1976 Braun .................. C06B 23/009
149/19.92

* cited by examiner

*Primary Examiner* — Paul A Zucker

(57) ABSTRACT

A compound of Formula I:

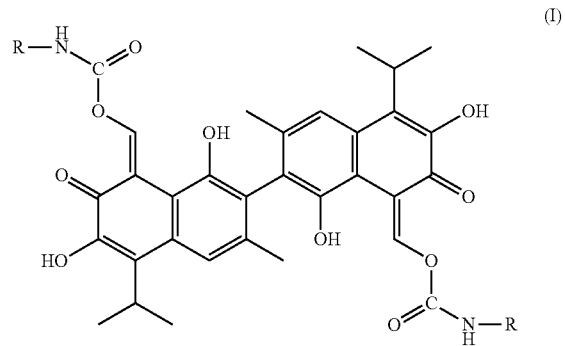

is disclosed. A method of preparing the compound of Formula I is also disclosed. R is alkyl, haloalkyl, aryl, or substituted aryl. Preferably, R is —$CH_3$, —$CH_2CH_3$, —$CH_2CH_2CH_3$, —$CH(CH_3)_2$, —$CH_2CH_2CH_2CH_3$, —$CF_3$, —$CHF_2$, —$CH_2CF_3$,

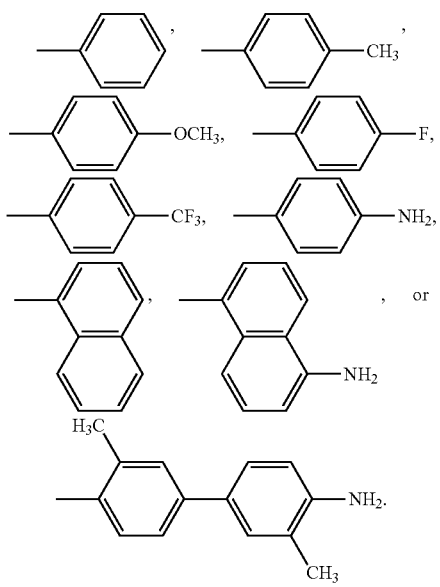

9 Claims, No Drawings

GOSSYPOL ISOCYANATE ESTER COMPOUNDS WITH ANTILEUKEMIC ACTIVITIES AND A METHOD OF PREPARING THE SAME

The present invention claims priority to Chinese Patent Application No. 202010654056.4, filed on Jul. 8, 2020, which is incorporated by reference for all purposes as if fully set forth herein.

BACKGROUND OF THE INVENTION

Field of the Invention

The present invention relates to the field of pharmaceutical chemistry, and in particular to gossypol isocyanate ester compounds with antileukemic activities and a method of preparing the same.

Discussion of the Related Art

Gossypol (compound of formula II) is a polyphenolic bis-naphthalene aldehyde compound, and a natural yellow pigment found in small cell glands between cotton cells. It is an inhibitor of the anti-apoptotic protein of the Bcl-2 family, not only effectively blocking the binding pocket of Bcl-2, Bcl.-xL and BH3, but also blockers binding to Mcl-1 (a homologous protein of Bcl-2).

Studies have shown that the aldehyde group at the 8,8'-position of gossypol is related to cytotoxicity. Isocyanate is a common chemical building block. The present application combines isocyanate and gossypol through an esterification reaction to reduce the toxicity of gossypol, and retains the biological activity of gossypol and obtains new gossypol isocyanate ester compounds with antileukemic activities.

SUMMARY OF THE INVENTION

In one embodiment, the present invention provides a compound of the following Formula I:

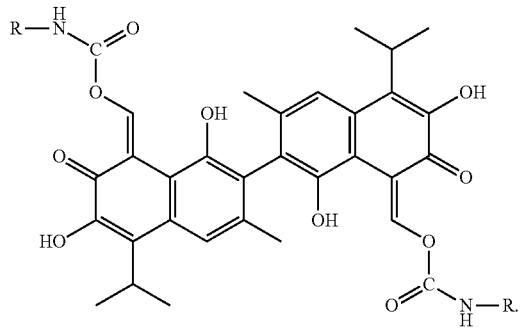

I

In Formula I, R is alkyl, haloalkyl, aryl, or substituted aryl.

In another embodiment, in Formula I, R is —CH$_3$, —CH$_2$CH$_3$, —CH$_2$CH$_2$CH$_3$, —CH(CH$_3$)$_2$, —CH$_2$CH$_2$CH$_2$CH$_3$, —CF$_3$, —CHF$_2$, —CH$_2$CF$_3$,

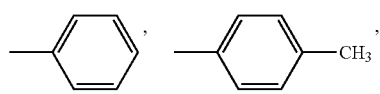

-continued

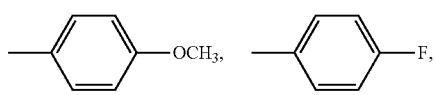

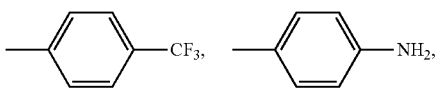

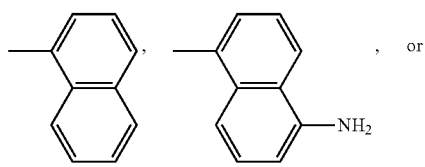

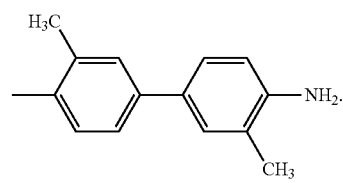

In another embodiment, the compound of Formula I is

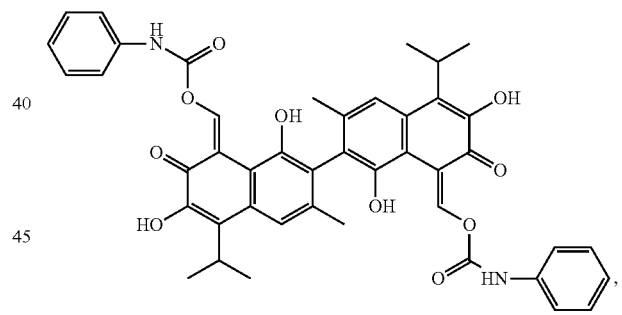

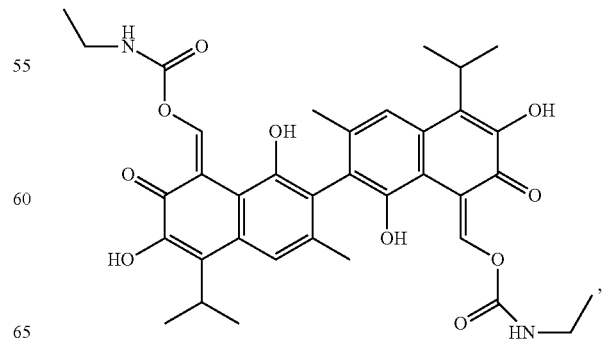

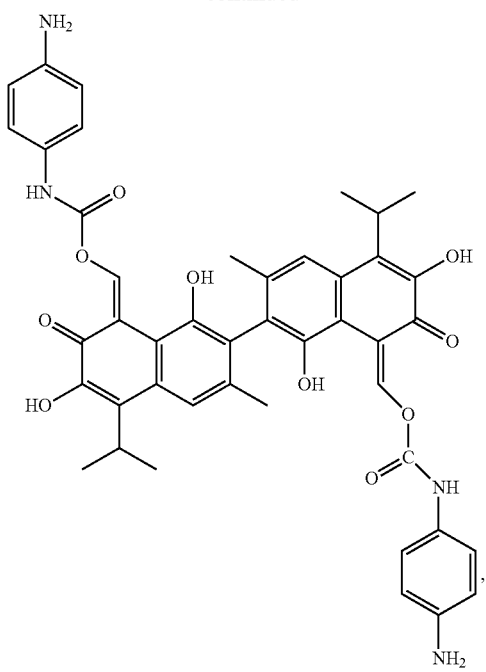

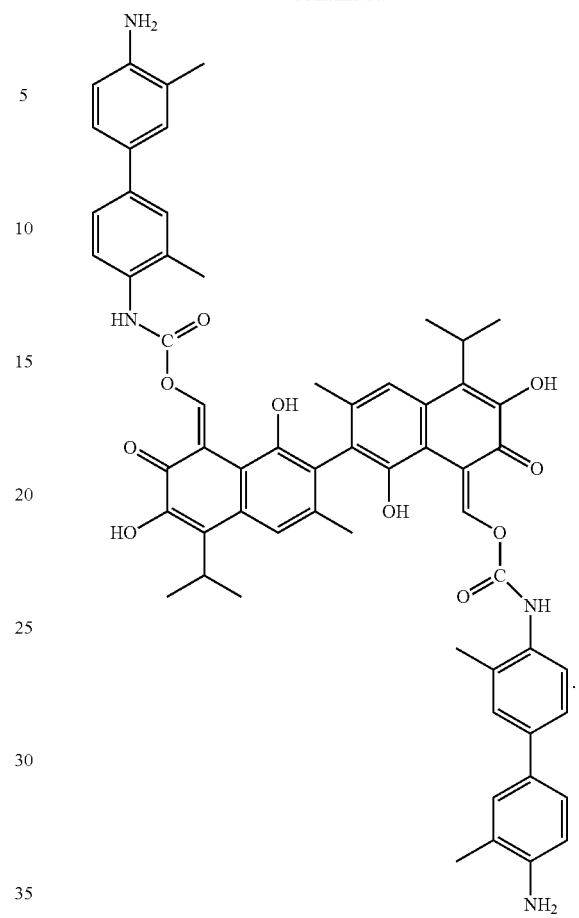

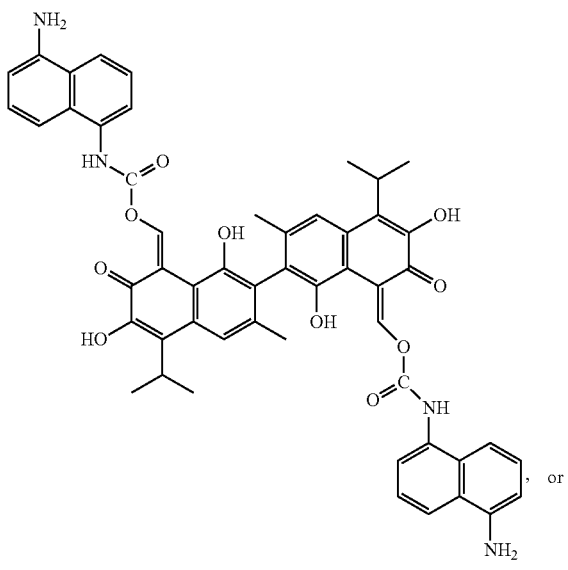

, or

In another embodiment, a method of preparing the compound of Formula I includes: (1) mixing a compound of Formula III and a compound of Formula II, in a molar ratio of 1:2 to 1:2.2, and a first solvent to form a mixture, and stirring and heating the mixture at 25-85° C. for 1-3 hours; (2) removing the first solvent to obtain a crude product; and (3) recrystallizing the crude product in a second solvent to obtain the compound of Formula I. In Formula I, R is alkyl, haloalkyl, aryl, or substituted aryl.

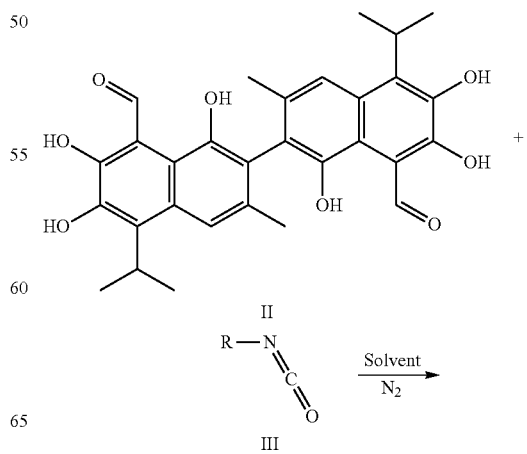

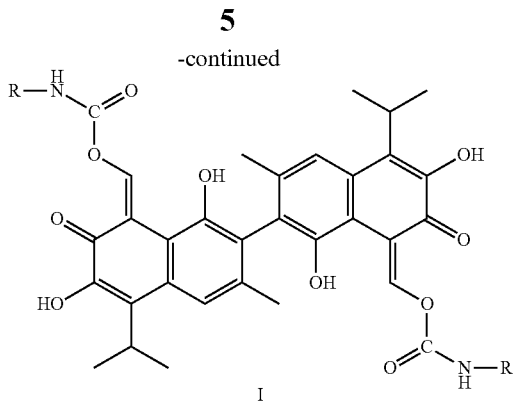

I

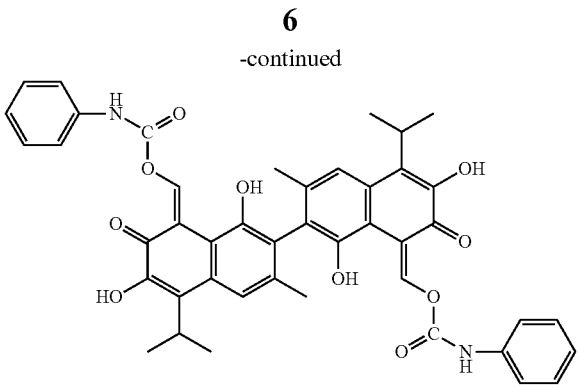

In another embodiment, the first solvent is dichloromethane, toluene, or acetonitrile.

In another embodiment, the first solvent is toluene.

In another embodiment, the molar ratio of the compound of Formula III and the compound of Formula II is 1:2.1.

In another embodiment, the mixture at 85° C. for 2 hours.

In another embodiment, the second solvent is a 1:1 mixture of methanol and acetone.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention.

Advantages of the present invention are: the inventors use gossypol as a key starting material, and combine gossypol with isocyanate to synthesize gossypol isocyanate ester compounds with antileukemic activities. The synthetic route is environmentally friendly, and has low production cost, high operation safety, and only one step. The starting raw are fully utilized. The synthetic method is suitable for industrial production.

Example 1: Preparing (1Z,1'Z)-(1,1',6,6'-tetrahydroxy-5,5'-diisopropyl-3,3'-dimethyl-7,7'-dioxo-[2,2'-binaphthal-ene]-8,8'(7H,7'H)-diylidene)bis(methanylylidene) bis(phenylcarbamate) (Compound 1)

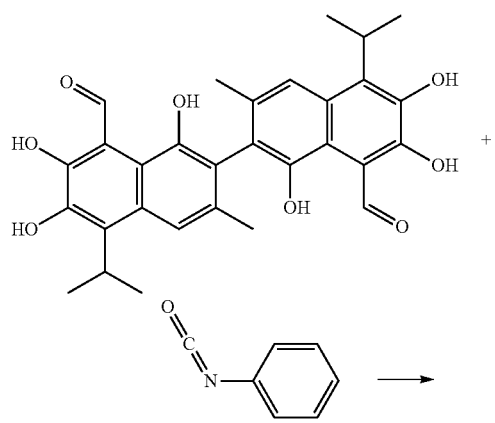

100 mg gossypol and 48.5 mg of phenyl isocyanate (a molar ratio of 1:2.1) were dissolved in 35 mL anhydrous toluene in 100 mL flask under nitrogen atmosphere to form a mixture. The mixture was stirred and heated at 85° C. After thin layer cohomotopy indicated that the reaction was complete, toluene was removed under reduced pressure to give a crude product. The crude product was added to 30 mL of 1:1 mixture of methanol for recrystallization. The recrystallization product was filtered, washed with 5 mL methanol, and dried to obtain 122.77 mg of the title compound, a yield of 84.12%.

$^1$H-NMR (400 MHz, DMSO-$d_6$) δ: 13.51 (2H, s, $C_{6,6'}$—OH), 9.91 (2H, s, $C_{11,11'}$—H), 8.81 (2H, m, $N_{17,17'}$—H), 7.54 (8H, d, $C_{19,20,22,23,19',20',22',23'}$—H), 7.28 (2H, s, $C_{21,21'}$—H), 7.21 (2H, s, $C_{4,4'}$—H), 7.15 (2H, s, $C_{1,1'}$—OH), 3.74 (2H, m, J=6.1 Hz, $C_{13,13'}$—H), 1.54 (6H, s, $C_{12,12'}$—H), 1.13 (12H, t, J=7.0 Hz, $C_{14,14',15,15'}$—H). $^{13}$C-NMR (100 MHz, DMSO-$d_6$) δ: 182.34, 169.32, 158.58, 154.80, 145.15, 139.04, 134.72, 125.50, 120.39, 118.15, 117.35, 26.87, 21.04, 14.54.

Example 2: Preparing (1Z,1'Z)-(1,1',6,6'-tetrahydroxy-5,5'-diisopropyl-3,3'-dimethyl-7,7'-dioxo-[2,2'-binaphtha-lene]-8,8'(7H,7'H)-diylidene)bis(methanylylidene) bis(ethylcarbamate) (Compound 2)

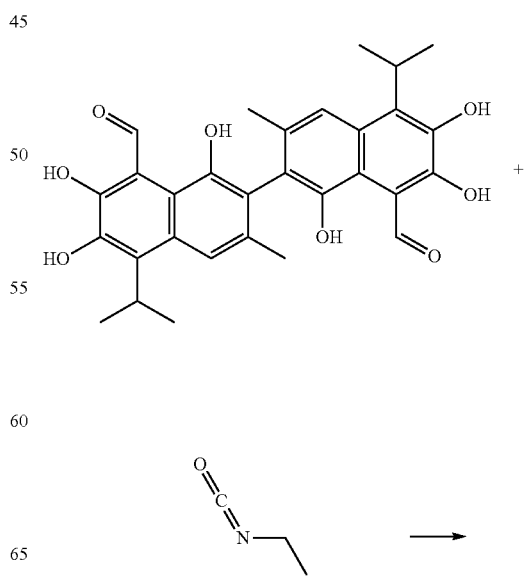

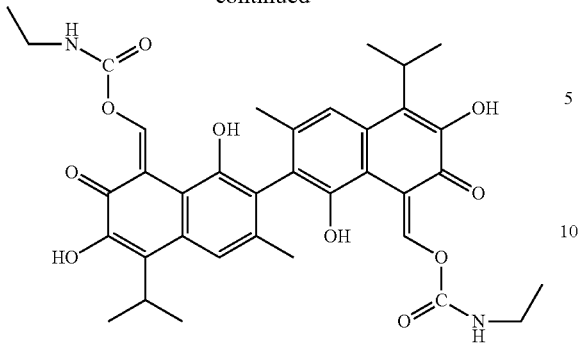

100 mg gossypol and 29 mg of ethyl isocyanate (a molar ratio of 1:2.1) were dissolved in 30 mL anhydrous toluene in 100 mL flask under nitrogen atmosphere to form a mixture. The mixture was stirred and heated at 85° C. After thin layer cohomotopy indicated that the reaction was complete, toluene was removed under reduced pressure to give a crude product. The crude product was added to 30 mL of 1:1 mixture of methanol for recrystallization. The recrystallization product was filtered, washed with 5 mL methanol, and dried to obtain 106.94 mg of the title compound, a yield of 83.93%.

$^1$H-NMR (400 MHz, DMSO-$d_6$) δ: 13.34 (2H, s, $C_{6,6'}$—OH), 9.88 (2H, s, 7.68 (2H, d, $N_{17,17'}$—H), 7.38 (2H, s, $C_{4,4'}$—H), 7.28 (2H, s, $C_{1,1'}$—OH), 3.67 (2H, m, $C_{13,13'}$—H), 3.02 (4H, d, $C_{18,18'}$—H), 2.15 (6H, s, $C_{12,12'}$—H), 1.54 (6H, t, $C_{19,19'}$—H), 1.27 (12H, s, $C_{14,14',15,15'}$—H). $^{13}$C-NMR (100 MHz, DMSO-$d_6$) δ: 179.77, 172.16, 152.76, 148.52, 131.00, 129.40, 128.97, 126.48, 120.79, 117.14, 99.33, 98.53, 29.88, 23.65, 22.95, 20.22, 14.72.

Example 3: Preparing ((8Z,8'Z)-1,1',6,6'-tetrahydroxy-5,5'-diisopropyl-3,3'-dimethyl-7,7'-dioxo-[2,2'-binaphthalene]-8,8'(7H,7'H)-diylidene)bis(methaneylylidene) bis((4-aminophenyl)carbamate) (Compound 3)

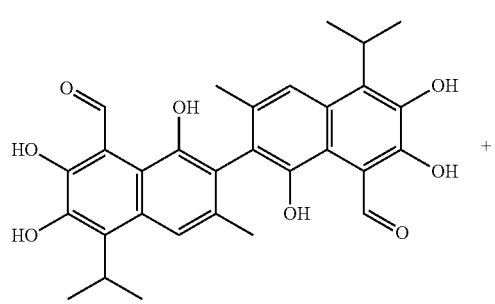

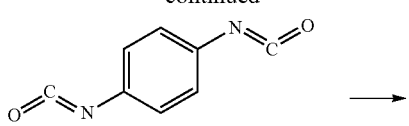

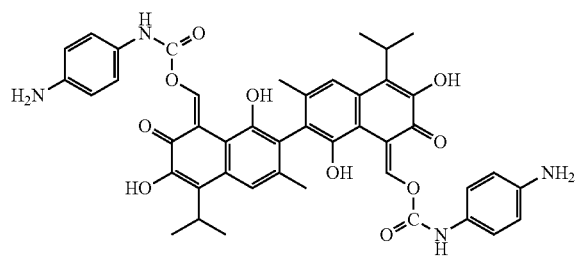

100 mg gossypol and 65 mg of 1,4-phenylene diisocyanate (a molar ratio of 1:2.1) were dissolved in 30 mL anhydrous toluene in 100 mL flask under nitrogen atmosphere to form a mixture. The mixture was stirred and heated at 85° C. After thin layer cohomotopy indicated that the reaction was complete, toluene was removed under reduced pressure to give a crude product. The crude product was added to 30 mL of 1:1 mixture of methanol for recrystallization. The recrystallization product was filtered, washed with 5 mL methanol, and dried to obtain 132.10 mg of the title compound, a yield of 78.30%.

$^1$H-NMR (400 MHz, DMSO-$d_6$) δ: 14.68 (1H, s, $C_{6,6'}$—OH), 10.04 (2H, d, J=13.2 Hz, $C_{11,11'}$—H), 9.51 (4H, s, $N_{23,23'}$—H), 8.46 (2H, s, $C_{24,24'}$—H), 7.36 (8H, s, $C_{19,20,21,22,19',20',21',22'}$—H), 7.24 (2H, s, $C_{4,4'}$—H), 6.99 (1H, s, $C_1$—OH), 6.90 (1H, s, $C_{1'}$—OH), 3.82-3.70 (2H, m, $C_{13,13'}$—H), 2.21 (3H, s, $C_3$—H), 2.10 (2H, s, $C_{3'}$—H), 1.46 (12H, s, $C_{14,15,14',15'}$—H). $^{13}$C-NMR (100 MHz, DMSO-$d_6$) δ: 178.40, 167.02, 158.31, 154.78, 147.89, 140.73, 133.83, 129.27, 123.90, 123.59, 121.40, 118.40, 21.40, 20.69, 14.02.

Example 4: Preparing ((8Z,8'Z)-1,1',6,6'-tetrahydroxy-5,5'-diisopropyl-3,3'-dimethyl-7,7'-dioxo-[2,2'-binaphthalene]-8,8'(7H,7'H)-diylidene)bis(methaneylylidene) bis((5-aminonaphthalen-1-yl)carbamate) (Compound 4)

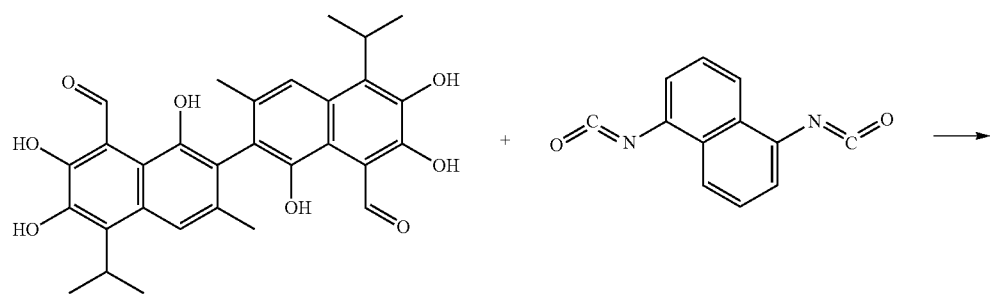

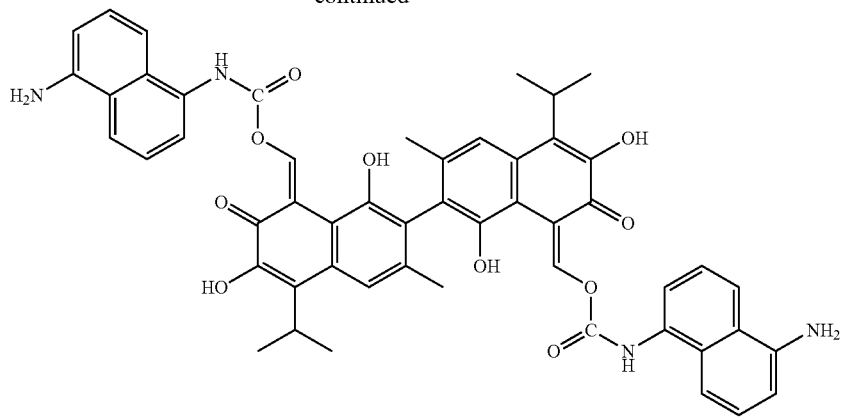

100 mg gossypol and 85 mg of 1,5-naphthalene diisocyanate (a molar ratio of 1:2.1) were dissolved in 30 mL anhydrous toluene in 100 mL flask under nitrogen atmosphere to form a mixture. The mixture was stirred and heated at 85° C. After thin layer cohomotopy indicated that the reaction was complete, toluene was removed under reduced pressure to give a crude product. The crude product was added to 30 mL of 1:1 mixture of methanol for recrystallization. The recrystallization product was filtered, washed with 5 mL methanol, and dried to obtain 139.73 mg of the title compound, a yield of 74.32%.

$^1$H-NMR (400 MHz, DMSO-d$_6$) δ: 14.74 (2H, s, C$_{6,6'}$—OH), 11.12 (2H, s, C$_{11,11'}$—H), 10.52 (2H, s, N$_{28,28'}$—H), OH), 6.90 (1H, s, C$_{3'}$—OH), 3.73 (2H, s, C$_{13,13'}$—OH), 2.30 (3H, s, C$_3$—H), 2.23 (3H, s, C$_{3'}$—H), 1.47 (12H, s, C$_{14,15,14',15'}$—H). $^{13}$C-NMR (100 MHz, DMSO-d$_6$) δ: 170.68, 167.53, 165.43, 153.06, 151.36, 144.05, 142.64, 137.01, 130.18, 121.53, 119.96, 107.58, 60.14, 20.96, 14.49.

Example 5: Preparing ((8Z,8')-1,1',6,6'-tetrahydroxy-5,5'-diisopropyl-3,3'-dimethyl-7,7'-dioxo-[2,2'-binaphthalene]-8,8'(7H,7'H)-diylidene)bis(methaneylylidene) bis((4'-amino-3,3'-dimethyl-[1,1'-biphenyl]-4-yl)carbamate) (Compound 5)

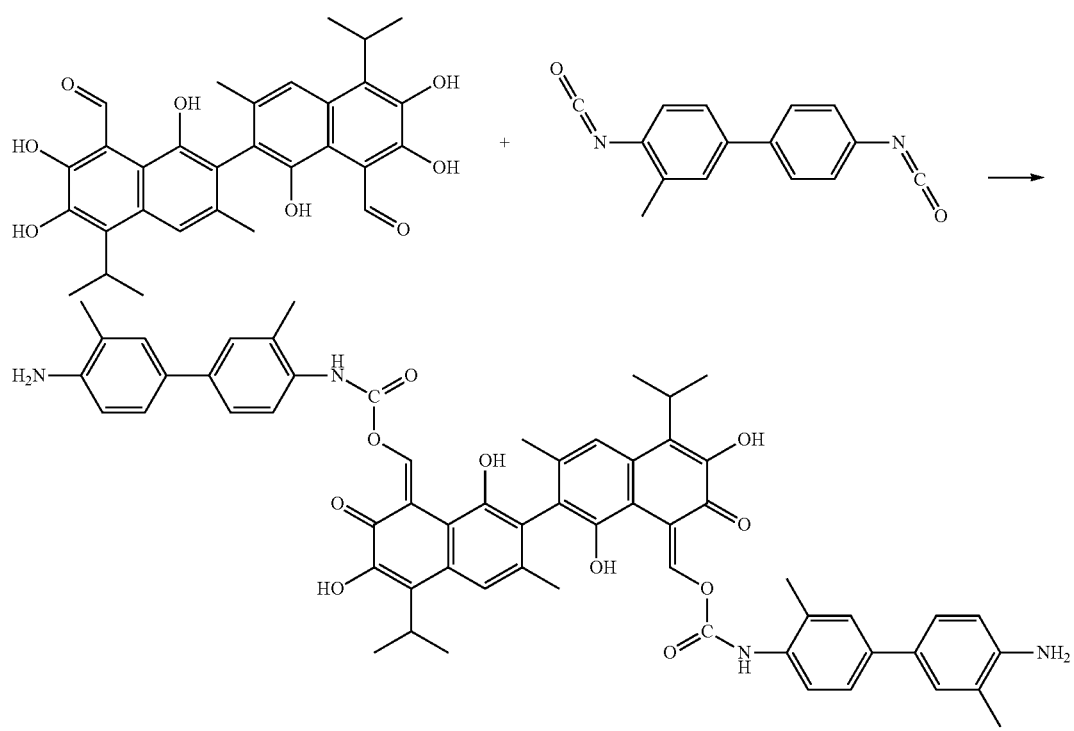

10.13 (2H, s, C$_{17,17'}$—NH), 8.50 (1H, s, C$_{29'}$—OH), 8.29 (1H, s, C$_{29}$—OH), 7.61 (4H, d, J=7.0 Hz, C$_{20,23,20',2''}$—H), 7.48-7.31 (m, 6H, C$_{21,24,25,21',24',25'}$—H), 7.24 (2H, 1,$_{4,4'}$—H), 7.17 (2H, d, J=7.2 Hz, C$_{19,19'}$—H), 6.97 (1H, s, C$_{3'}$—

100 mg gossypol and 107 mg of 4,4'-diisocyanato-3,3'-dimethylbiphenyl (a molar ratio of 1:2.1) were dissolved in 40 mL anhydrous toluene in 100 mL flask under nitrogen atmosphere to form a mixture. The mixture was stirred and heated at 85° C. After thin layer cohomotopy indicated that the reaction was complete, toluene was removed under reduced pressure to give a crude product. The crude product was added to 30 mL of 1:1 mixture of methanol for recrystallization. The recrystallization product was filtered, washed with 5 mL methanol, and dried to obtain 159.83 mg of the title compound, a yield of 76.52%.

$^1$H-NMR (400 MHz, DMSO-$d_6$) δ: 13.99 (2H, s, $C_{6,6'}$—OH), 12.00 (2H, s, $C_{11,11'}$—H), 10.13 (2H, s, $C_{32,32'}$—H), 9.63 (2H, s, $N_{17,17'}$—H), 8.50 (2H, s, $C_{33,33'}$—H), 7.58 (12H, dd, J=56.7, 48.4 Hz, $C_{25,28,29,25',28',29'}$—H), 7.25 (2H, s, $C_{4,4'}$—H), 7.01 (2H, s, $C_{1,1'}$—OH), 3.72 (1H, s, J=30.2 Hz, $C_{13,13'}$—H), 2.26 (12H, d, J=22.9 Hz, $C_{30,30',31,31'}$—H), 2.15 (6H, s, $C_{2,12'}$—H), 1.49 (12H, s, $^{13}$C-NMR (100 MHz, DMSO-$d_6$) δ: 194.33, 178.77, 162.90, 151.46, 145.93, 138.09, 124.95, 113.23, 109.80, 108.09, 106.68, 25.06, 22.40, 16.43, 15.01.

Example 6: CCK8 Method to Detect the Growth Inhibitory Effect of Gossypol Isocyanate Ester Compounds on Three Kinds of Leukemia Cells Cell lines: Jurkat (acute T-cell leukemia), HL-60 (human promyelocytic leukemia cells), K-562 (chronic myeloid leukemia), provided by the Affiliated Hospital of Guangdong Medical College. The cells were cultured in RPMI1640 medium containing 10% fetal bovine serum, penicillin 100 U/L, streptomycin 100 mg/L, 37° C., 5% $CO_2$, saturated humidity incubator, and the logarithmic growth phase cells were tested.

Drugs: Imatinib solution and 5 compound solutions (compounds 1-5) were prepared with physiological saline, and the final drug concentration were 1, 5, 10, 50, 100 μMol/L.

Test method: The logarithmic growth phase leukemia cell lines were taken, counted, and inoculated on a 96-well culture plate at a density of $1 \times 10^5$/mL, 100 μL per well. After 24 hours of cultivation, 100 μL of double-concentration medium containing different concentrations of compounds was added to each well. The medium containing the highest concentration of DMSO was used as the solvent control. After 48 hours of drug action, 20 μL of CCK8 color developing solution was added to each well, and the color was developed at 37° C. The OD450 was measured with a microplate reader until the absorbance was about 1.5. The inhibition rate was calculated using the formula:

Inhibition Rate (%)=(1−Absorbance Value of Administration Group/Absorbance Value of Control Group)×100%

The half-inhibitory concentration of cells ($IC_{50}$) was calculated by the Kou's method. The results are shown in Table 1.

TABLE 1

The Inhibitory Effects of Gossypol Isocyanate Ester Compounds on Three Leukemia Cell Lines

| Compounds | $IC_{50}$ (μmol/L) | | |
|---|---|---|---|
|  | Jurkat | HL-60 | K562 |
| Imatinib | 2.75 | 0.24 | 0.16 |
| Compound 1 | 18.27 | 31.65 | 37.11 |
| Compound 2 | 68.24 | 92.18 | 49.11 |
| Compound 3 | 12.98 | 26.61 | 16.32 |
| Compound 4 | 21.72 | 15.91 | 21.68 |
| Compound 5 | 32.63 | 28.36 | 48.83 |

The test results showed that the gossypol isocyanate ester compounds have good anti-leukemia activity in the three cell lines tested. Compound 3 has the best activity, and is active against all three cell lines. The above experimental results indicate that the compounds of the present invention have good anti-leukemia activity, and can be used as candidate compounds or lead compounds for further research on the development of anti-leukemia medications.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A compound of the following Formula I:

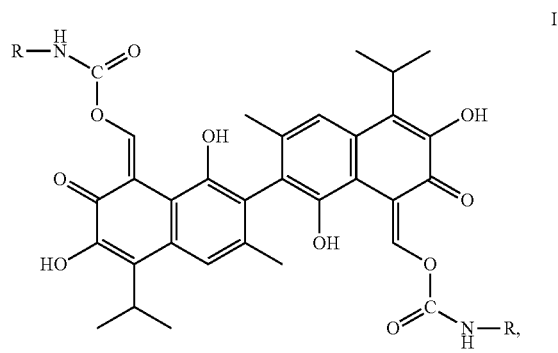

wherein R is alkyl, haloalkyl, aryl, or substituted aryl.

2. The compound of claim 1, wherein R is —$CH_3$, —$CH_2CH_3$, —$CH_2CH_2CH_3$, —$CH(CH_3)_2$, —$CH_2CH_2CH_2CH_3$, —$CF_3$, —$CHF_2$, —$CH_2CF_3$,

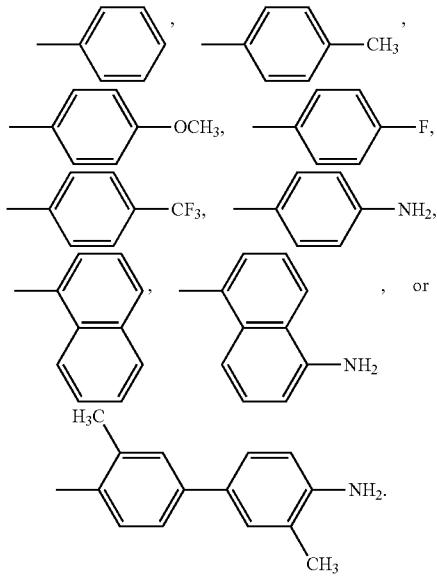

3. The compound of claim 1, wherein the compound of Formula I is
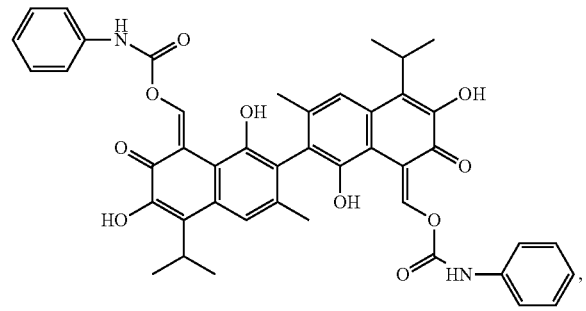
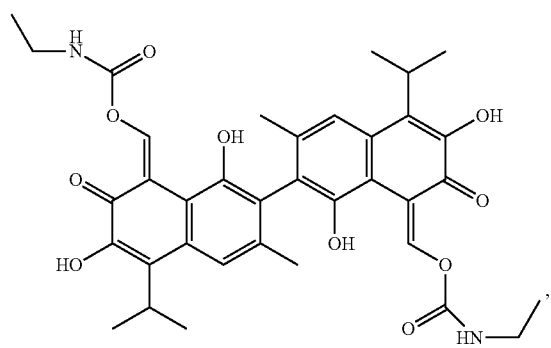
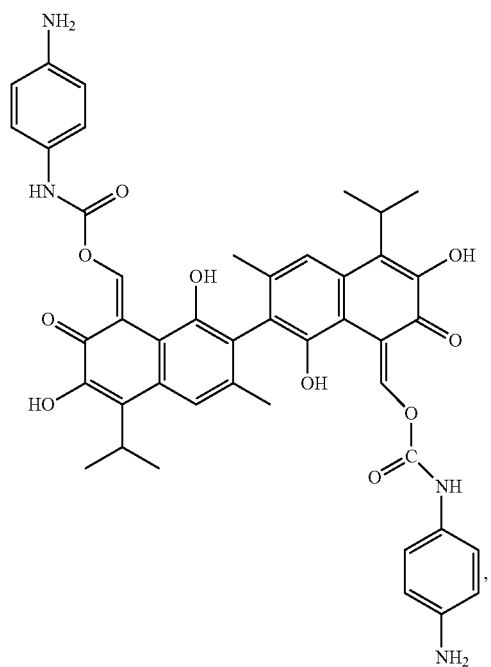
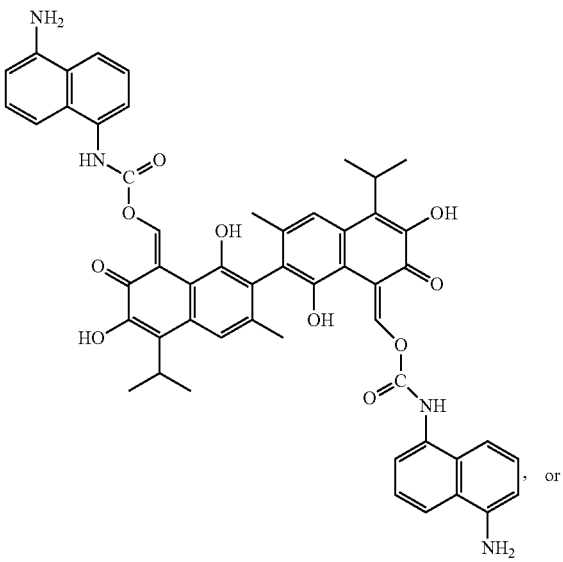
, or
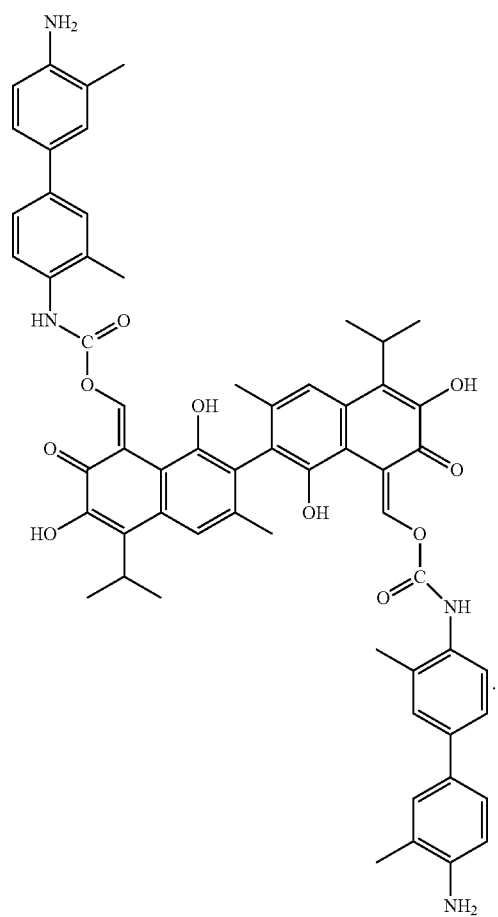

4. A method of preparing a compound of Formula I, comprising:

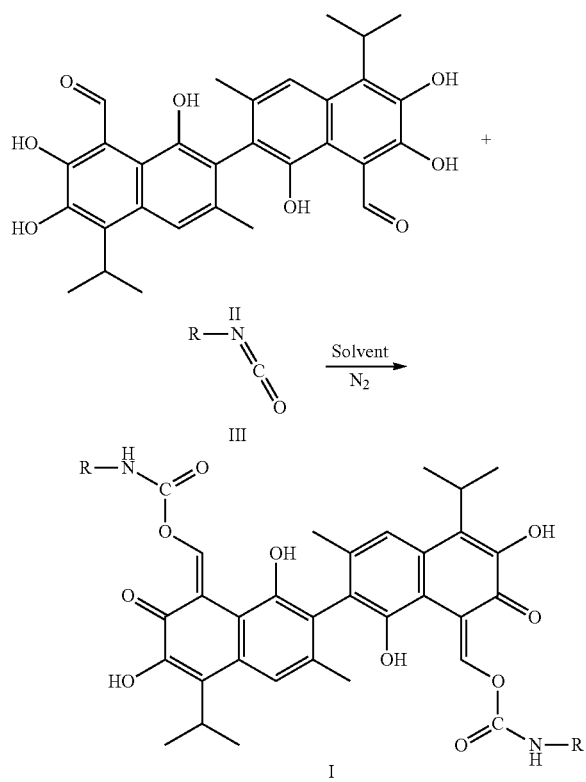

(1) mixing a compound of Formula III and a compound of Formula II, in a molar ratio of 1:2 to 1:2.2, and a first solvent to form a mixture, and stirring and heating the mixture at 25-85° C. for 1-3 hours;

(2) removing the first solvent to obtain a crude product; and (3) recrystallizing the crude product in a second solvent to obtain the compound of Formula I, wherein R is alkyl, haloalkyl, aryl, or substituted aryl.

5. The method of claim 4, wherein the first solvent is dichloromethane, toluene, or acetonitrile.

6. The method of claim 5, wherein the first solvent is toluene.

7. The method of claim 4, wherein the molar ratio of the compound of Formula III and the compound of Formula II is 1:2.1.

8. The method of claim 4, wherein the mixture is heated at 85° C. for 2 hours.

9. The method of claim 4, wherein the second solvent is a 1:1 mixture of methanol and acetone.

* * * * *